United States Patent
Dinh et al.

(10) Patent No.: US 11,957,560 B2
(45) Date of Patent: Apr. 16, 2024

(54) IMPLANT LEAFLET PROTECTION ASSEMBLY AND METHOD

(71) Applicant: Medtronic Vascular, Inc., Santa Rosa, CA (US)

(72) Inventors: Thuy Linh Dinh, Santa Rosa, CA (US); Alkindi Kibria, Santa Rosa, CA (US); Victoria Ung, Santa Rosa, CA (US); Veronica Woen, Santa Rosa, CA (US); Priyanka Ganesh, Santa Rosa, CA (US); Kshitija Garde, Santa Rosa, CA (US)

(73) Assignee: Medtronic Vacular, Inc., Santa Rosa, CA (US)

( * ) Notice: Subject to any disclaimer, the term of this patent is extended or adjusted under 35 U.S.C. 154(b) by 202 days.

(21) Appl. No.: 17/545,882

(22) Filed: Dec. 8, 2021

(65) Prior Publication Data
US 2023/0172701 A1 Jun. 8, 2023

(51) Int. Cl.
*A61F 2/24* (2006.01)
*A61F 2/00* (2006.01)
*A61F 2/95* (2013.01)

(52) U.S. Cl.
CPC .......... *A61F 2/0095* (2013.01); *A61F 2/2418* (2013.01); *A61F 2/2427* (2013.01); *A61F 2/9522* (2020.05); *A61F 2240/001* (2013.01)

(58) Field of Classification Search
CPC .... A61F 2/0095; A61F 2/2418; A61F 2/2427; A61F 2/9522
See application file for complete search history.

(56) References Cited

U.S. PATENT DOCUMENTS

2018/0133000 A1* 5/2018 Scheinblum .......... A61F 2/2412

* cited by examiner

*Primary Examiner* — Suba Ganesan
(74) *Attorney, Agent, or Firm* — Medler Ferro Woodhouse & Mills PLLC

(57) ABSTRACT

An assembly includes a medical device having a stent and a prosthetic valve connected to the stent. The prosthetic valve includes valve leaflets. The assembly further includes a buffer piece having a leaflet cover and a removable attaching structure. The leaflet cover protects the valve leaflets and the removable attaching structure removably attaches the buffer piece to the medical device. The buffer piece prevents contact, imprinting, abrasion, and/or damage to the valve leaflets.

23 Claims, 5 Drawing Sheets

IMPLANT LEAFLET PROTECTION ASSEMBLY AND METHOD

FIELD

The present technology is generally related to medical device protection systems and methods.

BACKGROUND

Medical devices, including, but not limited to, stents, prosthetic valves, and other implantable medical devices, can be compressed to facilitate delivery of such medical devices at one or more implantation sites in the body of a subject, e.g., a native cardiac valve, or the like. Each medical device is delivered to an implantation site using a delivery device such as a catheter, for example, that has radial dimensions that are smaller than the unconstrained or expanded radial dimensions of the medial device and/or that are smaller than the dimensions of the medical device upon deployment of the medical device at the implantation site. To facilitate insertion of such a medical device into or on the delivery device, the medical device is compressed, typically, at least radially. Such radial compression is known as crimping.

However, up to and including crimping, the medical device can be subject to damage, e.g., damage to valve leaflets of the implants, or the like. Such damage might include, without limitation, damage during manufacturing, treatment, shipping, storage/aging, and crimping. The damage produced from such action can result in long term durability issues for the medical device and its functionality.

SUMMARY

The techniques of this disclosure generally relate to an assembly includes a medical device having a stent and a prosthetic valve connected to the stent. The prosthetic valve includes valve leaflets. The assembly further includes a buffer piece having a leaflet cover and a removable attaching structure. The leaflet cover protects the valve leaflets and the removable attaching structure removably attaches the buffer piece to the medical device. The buffer piece prevents contact, imprinting, abrasion, and/or damage to the valve leaflets.

In one aspect, the present disclosure provides a buffer piece. The buffer piece includes a leaflet cover configured to protect valve leaflets of a medical device. The buffer piece further includes a removable attaching structure configured to removably attach the buffer piece to the medical device.

In another aspect, the present disclosure provides a method including removably attaching a buffer piece to a medical device. The buffer piece holds valve leaflets of the medical device in place.

The details of one or more aspects of the disclosure are set forth in the accompanying drawings and the description below. Other features, objects, and advantages of the techniques described in this disclosure will be apparent from the description and drawings, and from the claims.

DETAILED DESCRIPTION

Figure 1:
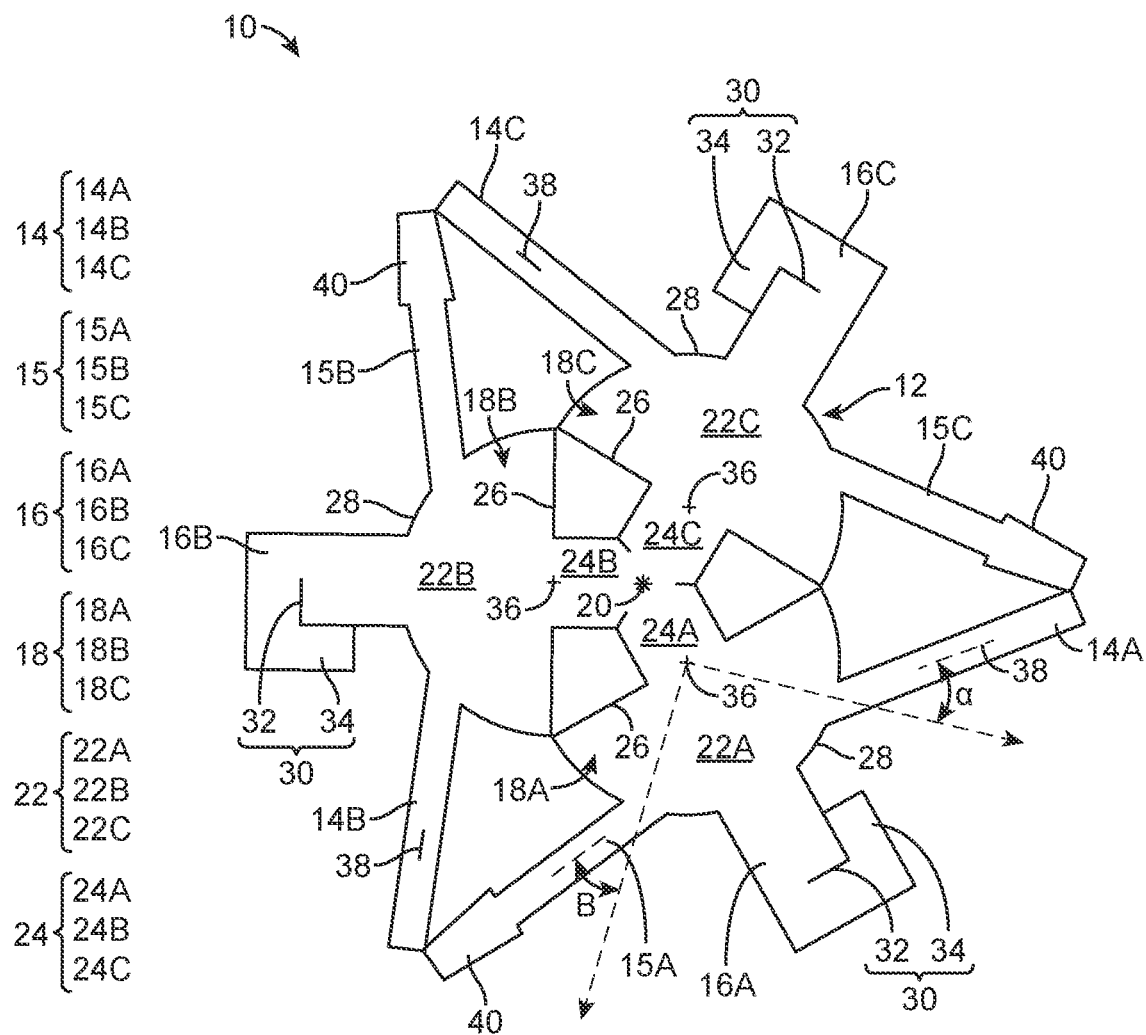
FIG. 1 is a top plan view of a buffer piece in accordance with one embodiment.
Figure 2:
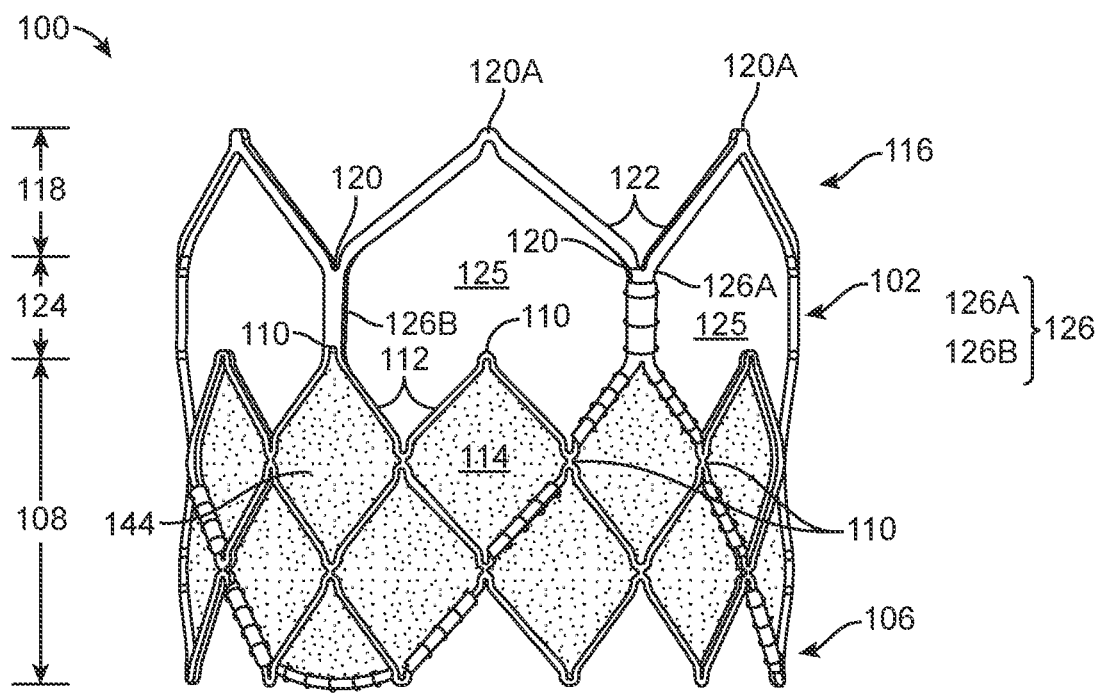
FIG. 2 is a side view of a transcatheter valve prosthesis in an expanded configuration for use with the buffer piece of FIG. 1 in accordance with one embodiment.
Figure 3:
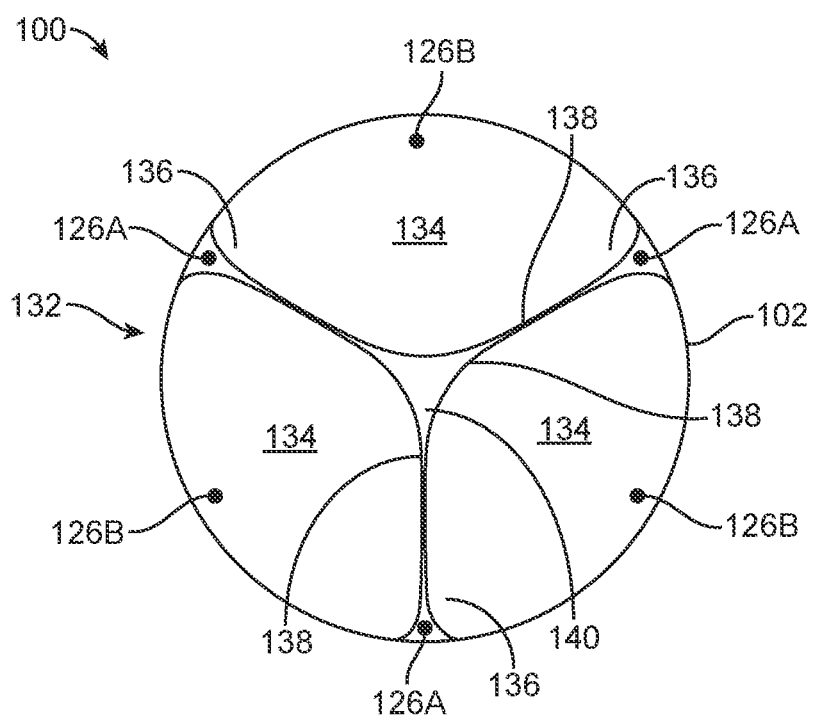
FIG. 3 is an end view of the transcatheter valve prosthesis of FIG. 2 in accordance with one embodiment.
Figure 4:
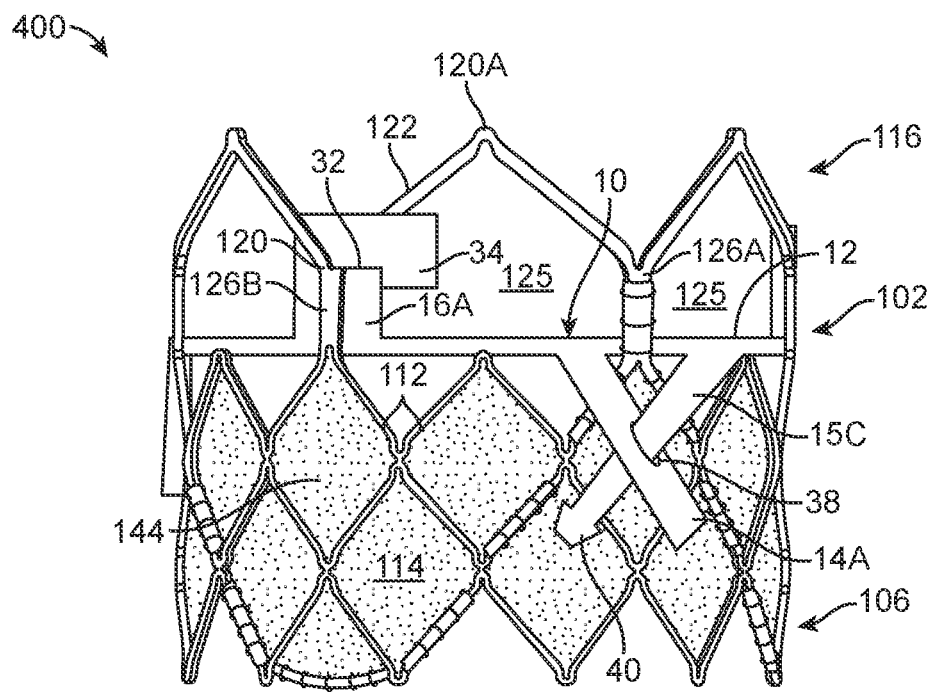
FIG. 4 is a side view of an implant leaflet protection assembly including the transcatheter valve prosthesis of FIG. 2 having the buffer piece of FIG. 1 attached in accordance with one embodiment.
Figure 5:
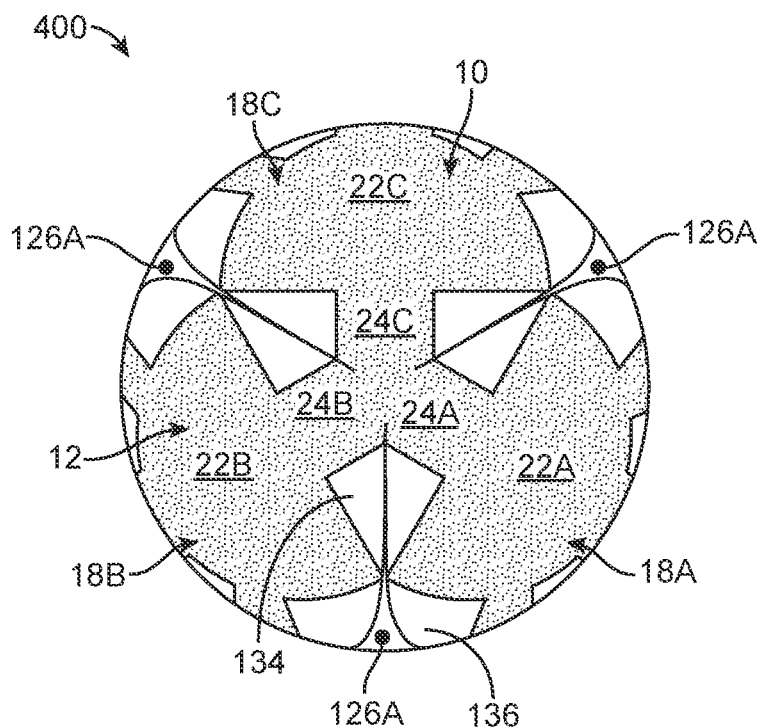
FIG. 5 is an end view of the implant leaflet protection assembly of FIG. 4 including the transcatheter valve prosthesis of FIG. 3 having the buffer piece of FIG. 1 attached in accordance with one embodiment.

FIG. 1 is a top plan view of a buffer piece 10 in accordance with one embodiment. FIG. 2 is a side view of a transcatheter valve prosthesis 100 in an expanded configuration for use with buffer piece 10 of FIG. 1 in accordance with one embodiment. FIG. 3 is an end view of transcatheter valve prosthesis 100 of FIG. 2 in accordance with one embodiment. FIG. 4 is a side view of an implant leaflet protection assembly 400 including transcatheter valve prosthesis 100 of FIG. 2 having buffer piece 10 of FIG. 1 attached in accordance with one embodiment. FIG. 5 is an end view of implant leaflet protection assembly 400 of FIG. 4 including transcatheter valve prosthesis 100 of FIG. 3 having buffer piece 10 of FIG. 1 attached in accordance with one embodiment.

Paying particular attention to FIG. 1, buffer piece 10 includes a leaflet cover 12, complementary attaching arms 14, 15, and stent anchor arms 16. Attaching arms 14, 15 are sometimes called first and second attaching arms 14, 15. More particularly, attaching arms 14, 15 include three attaching arms 14A, 14B, 14C, and 15A, 15B, and 15C, respectively. Stent anchor arms 16 include three stent anchor arms 16A, 16B, 16C.

In accordance with one embodiment, buffer piece 10 is integral, i.e., a single piece and not a plurality of separate pieces connected together. For example, buffer piece 10 is formed, e.g., cut, from bovine pericardium, polyethylene terephthalate (PET), silicone, mylar, polymer, or other biocompatible material. Buffer piece 10 has a minimal thickness, e.g., less than a thickness of the valve leaflets of transcatheter valve prosthesis 100 to minimize the impact to the profile at the outflow during crimping. Further, buffer piece 10 is flexible and conforms during crimping and can easily be retracted after crimp/final crimp as discussed below.

In accordance with this embodiment, leaflet cover 12 includes leaflet flaps 18. More particularly, leaflet flaps 18 include three leaflet flaps 18A, 18B, and 18C connected together at a center point 20 of buffer piece 10 and leaflet cover 12. Leaflet flaps 18 includes leaflet scallops 22 and leaflet scallop bridges 24. More particularly, leaflet flaps 18A, 18B, and 18C include leaflet scallops 22A, 22B, 22C and leaflet scallop bridges 24A, 24B, 24C, respectively.

In accordance with this embodiment, leaflet scallop 22A of leaflet flap 18A is a semicircle, i.e., half of a circle, having a base 26 and a semicircular circumference 28. Base 26, i.e., the diameter of the circle cut in half to form the semicircle, is perpendicular to a line radially extending from center point 20. Circumference 28, one half of the circumference of the circle cut in half to form the semicircle, is opposite center point 20 relative to base 26. Leaflet scallop bridge 24A extends radially inward to center point 20 from the center of base 26.

Stent anchor arm 16A extends radially outward from the center of circumference 28 in a direction opposite but parallel to leaflet scallop bridge 24A. Stent anchor arm 16A includes a stent attaching feature 30 at the end of stent anchor arm 16A. Stent attaching feature 30 includes a slot 32 and a tab 34 configured to removably attach around a strut of a stent of transcatheter valve prosthesis 100 as discussed further below.

Attaching arms 14A, 15A extend outward from circumference 28 on either side of stent anchor arm 16A. In the view of FIG. 1, stent anchor arm 16A is clockwise from attaching arm 14A on circumference 28 and attaching arm 15A is clockwise from stent anchor arm 16A on circumference 28.

Leaflet scallop 22A includes a center 36 at the center of base 26, i.e., center 36 is the center of the circle cut in half to form the semicircle of leaflet scallop 22A. An angle α between a line radially extending from center 36 and stent anchor arm 14A is nonzero, i.e., stent anchor arm 14A extends non-radially from circumference 28. Similarly, angle β between a line radially extending from center 36 and stent anchor arm 15A is nonzero, i.e., stent anchor arm 15A extends non-radially from circumference 28. In one embodiment, angle α equals angle β although angles α, β are different in other embodiments. This non-radial arrangement of stent anchor arms 14A, 15A facilitates attachment to adjacent stent anchor arms 14, 15 as discussed further below.

Stent anchor arm 14A is generally a long rectangular member in this embodiment. Stent anchor arm 14A includes a longitudinal slot 38 extending in the length direction of stent anchor arm 14A in the center of the width of stent anchor arm 14A. Slot 38 is sized appropriately to accept the adjacent stent anchor arm 15C therein to attach stent anchor arms 14A, 15C together.

Stent anchor arm 15A includes a tapered tip 40 at the outermost end of stent anchor arm 15A. Tapered tip 40 facilitates insertion of stent anchor arm 15A into slot 38 of stent anchor arm 14B.

At center point 20, leaflet scallop bridges 24A, 24B, 24C join together to form buffer piece 10 as a single integral piece. Leaflet scallops 22 are not directly connected together to allow leaflet scallops 22 to spread apart from one another facilitating mounting to transcatheter valve prosthesis 100.

Although leaflet flap 18A has been described in detail, the description equally applies to the features of leaflet flaps 18B, 18C, and so the description is not repeated for clarity.

With reference to FIGS. 2 and 3, transcatheter valve prosthesis 100, sometimes called a medical device 100, includes a radially expandable stent 102 and a prosthetic valve 132. Stent 102, sometimes called a frame 102, is generally tubular, and is mechanically or balloon expandable, having a crimped configuration for delivery within a vasculature and an expanded configuration for deployment within a native heart valve. When transcatheter valve prosthesis 100 is deployed within the valve annulus of a native heart valve, stent 102 of transcatheter valve prosthesis 100 is configured to be radially expanded within native valve leaflets of the patient's defective valve, to thereby retain the native valve leaflets in a permanently open state. In some embodiments, transcatheter valve prosthesis 100 is configured for replacement for an aortic valve such that an inflow end 106 of transcatheter valve prosthesis 100 extends into and anchors within the aortic annulus of a patient's left ventricle, while an outflow end 116 of transcatheter valve prosthesis 100 is positioned within the aortic sinuses.

Stent 102 of transcatheter valve prosthesis 100 may be a unitary frame or scaffold that supports prosthetic valve 132 including one or more valve leaflets 134 within the interior of stent 102. Prosthetic valve 132 is capable of blocking flow in one direction to regulate flow there-through via valve leaflets 134 that may form a bicuspid or tricuspid replacement valve.

The end view of FIG. 3 is taken from outflow end 116 and illustrates an exemplary tricuspid valve having three valve leaflets 134, although a bicuspid leaflet configuration may alternatively be used in some embodiments. More particularly, as transcatheter valve prosthesis 100 is configured for placement within a native aortic valve which typically has three leaflets, prosthetic valve 132 may include three valve leaflets 134. However, transcatheter valve prosthesis 100 is not required to have the same number of leaflets as the native valve. If transcatheter valve prosthesis 100 is alternatively configured for placement within a native valve having two leaflets such as the mitral valve, prosthetic valve 132 may include two or three valve leaflets. Although a particular transcatheter valve prosthesis 100 is set forth in accordance with one embodiment, generally transcatheter valve prosthesis 100 is representative of a medical device such as, but not limited to, surgical and transcatheter heart valves. Further, the number of leaflet flaps 18 including leaflet scallops 22 and leaflet scallop bridges 24 of buffer piece 10 matches the number of valve leaflets of prosthetic value 132.

Valve leaflets 134 may be attached to a graft material 144 which encloses or lines a portion of stent 102 as would be known to one of ordinary skill in the art of prosthetic tissue valve construction in light of this disclosure. Valve leaflets 134 are sutured or otherwise securely and sealingly attached along their bases to the interior surface of graft material 144, or otherwise attached to stent 102. Adjoining pairs of leaflets 134 are attached to one another at their lateral ends to form commissures 136, with free edges 138 of valve leaflets 134 forming coaptation edges that meet in area of coaptation 140.

Stent 102 will now be described in more detail. Stent 102 is a tubular component defining a central lumen or passageway, and defines inflow or proximal end 106 and outflow or distal end 116 of transcatheter valve prosthesis 100. Stent 102 may be formed by a laser-cut manufacturing method and/or another conventional stent forming method as would be understood by one of ordinary skill in the art in light of this disclosure.

As used herein, the proximal end of a prosthesis such as transcatheter valve prosthesis 100 is the end closest to the heart via the path of blood flow whereas the distal end is the end furthest away from the heart during deployment. In contrast and of note, the distal end of the catheter is usually identified to the end that is farthest from the operator/handle while the proximal end of the catheter is the end nearest the operator/handle.

For purposes of clarity of discussion, as used herein, the distal end of the catheter is the end that is farthest from the operator (the end furthest from the handle) while the distal end of transcatheter valve prosthesis 100 is the end nearest the operator (the end nearest the handle), i.e., the distal end of the catheter and the proximal end of transcatheter valve prosthesis 100 are the ends furthest from the handle while the proximal end of the catheter and the distal end of transcatheter valve prosthesis 100 are the ends nearest the handle. However, those of skill in the art will understand that depending upon the access location, transcatheter valve prosthesis 100 and the delivery system descriptions may be consistent or opposite in actual usage.

Stent 102 includes an inflow portion 108 at inflow end 106 of stent 102. Inflow portion 108 includes crowns 110 and struts 112 with each crown 110 being formed between a pair of opposing struts 112. Each crown 110 is a curved segment or bend extending between opposing struts 112. Inflow portion 108 is tubular, with a plurality of side openings 114 being defined by crowns 110 and struts 112.

Stent 102 further includes an outflow portion 118 at outflow end 116 of stent 102. Outflow portion 118 includes crowns 120 and struts 122 with each crown 120 being formed between a pair of opposing struts 122. Each crown 120 is a curved segment or bend extending between opposing struts 122. Outflow portion 118 can be configured in a shape that forms a central lumen or passageway, for example, a ring. A series of endmost outflow crowns 120A are formed at outflow end 116 of stent 102.

Stent 102 further includes a transition portion 124 that bridges, connects, or otherwise extends between inflow portion 108 and outflow portion 118. In some instances, transition portion 124 includes a total of six axial frame members 126, each axial frame member 126 extending between a crown 120 of outflow portion 118 and a crown 110 of inflow portion 108.

More particularly, each axial frame member 126 is an axial segment having a first end connected to a crown 120 of outflow portion 118 and a second end connected to a crown 110 of inflow portion 108. Axial frame members 126 are substantially parallel to the central longitudinal axis of stent 102. Each axial frame member 126 is disposed approximately halfway between a pair of adjacent endmost outflow crowns 120A. Three of the six axial frame members 126 are commissure posts 126A and aligned with and attached to a respective commissure 136 of the three valve leaflets 134 of prosthetic valve 132. Three of the axial frame members 126 are axial struts 126B and are disposed between adjacent commissure posts 126A.

In this embodiment, endmost outflow crowns 120A are not directly connected to axial frame members 126 of transition portion 124, but rather may be considered to be free or unattached while the remaining outflow crowns 120 of outflow portion 118 are directly connected to axial frame members 126 and disposed closer to inflow end 106 than endmost outflow crowns 120A.

Prosthetic valve 132 is disposed within and secured to at least transition portion 124 of stent 102 at commissure posts 126A. In addition, prosthetic valve 132 may also be disposed within and secured to inflow portion 108 of stent 102. Although one arrangement of securing prosthetic valve 132 is illustrated in FIG. 3, prosthetic valve 132 is secured in other arrangements in other embodiments.

Paying particular attention now to FIGS. 4 and 5 together, buffer piece 10 is attached to transcatheter valve prosthesis 100. In accordance with this embodiment, to attach buffer piece 10 to transcatheter valve prosthesis 100, attaching arms 14, 15 extend from within the interior of stent 102 through openings 125 of stent 102 and are coupled together at an exterior of stent 102. Further, stent anchor arms 16 are coupled to stent 102, e.g., to prevent buffer piece 10 from moving up.

More particularly, attaching arms 14, 15 are located on either side of a respective commissure post 126A and extend through openings 125 of stent 102. More particularly, stent 102 includes a series of six endmost outflow side openings 125 formed at outflow portion 118 and transition portion 124 of stent 102. Each opening 125 defines an open space in stent 102, which is formed in any type of shape, in the radially expanded configuration. In this embodiment, each endmost outflow side opening 125 is defined by two adjacent struts 122 of outflow portion 118, four adjacent struts 112 of inflow portion 108, and two adjacent axial frame members 126 of transition portion 124.

Attaching arms 14, 15 extend proximally from leaflet cover 12 to be directly adjacent to the exterior of struts 112. Tapered tips 40 of attaching arms 15 are passed through respective slots 38 in attaching arms 14. This couples attaching arms 15 to attaching arms 14 in a removal manner.

Further, stent anchor arms 16 extend distally from leaflet cover 12 to engage stent 102. More particularly, stent anchor arms 16 are aligned with and overlap axial struts 126B. At crowns 120, struts 122 of outflow portion 118 are placed within slots 32 of stent anchor arms 16. Tabs 34 of stent anchor arms 16 extend proximally from the respective struts 122 to ensure stent anchor arms 16 are couple to stent 102 in a robust yet removable manner.

As illustrated in FIG. 5, leaflet cover 12 covers valve leaflets 134. More particularly, each leaflet flap 18 covers a respective valve leaflet 134. Leaflet scallops 22 directly contact and/or protect valve leaflets 134 between commissures 136. Leaflet scallop bridges 24 cover coaptation 140. Leaflet cover 12 secures valve leaflets 134 in position, i.e., forces valve leaflets 134 down in the closed position, as well as provides a protective buffer piece that protects valve leaflets 134 from abrasive contact and damage from other structures such a leaflet protection tool or stent 102 as discussed further below.

In accordance with this embodiment, a portion of commissures 136 of valve leaflets 134 are exposed and not covered with leaflet flaps 18.

Although a specific removable attaching structure including attaching arms 14, 15 and stent anchor arms 16 of buffer piece 10 has been illustrated and described above, in an embodiment, the removable attaching structure of buffer piece 10 includes only stent anchor arms 16 for mounting buffer piece 10 to transcatheter valve prosthesis 100. In an embodiment, the removable attaching structure of buffer piece 10 includes only attaching arms 14, 15 for mounting buffer piece 10 to transcatheter valve prosthesis 100. In an embodiment, attaching arms 14, 15 are formed without slots 38/tapered tips 40 and are simply wrapped around stent 102 to removably attach buffer piece 10 to transcatheter valve prosthesis 100. In other embodiments, buffer piece 10 includes additional and/or different removable attaching structure(s), e.g., sutures, for removably attaching buffer piece 10 to transcatheter valve prosthesis 100.

Further, although a specific buffer piece 10 including leaflet cover 12 for securing and protecting valve leaflets 134 has been illustrated and described above, in an embodiment, leaflet cover 12 has additional and/or different features for securing and protecting valve leaflets 134. For example, additional and/or different features of leaflet covers are illustrated and described below in reference to FIGS. 8-10 in accordance with other embodiments.

Figure 6:
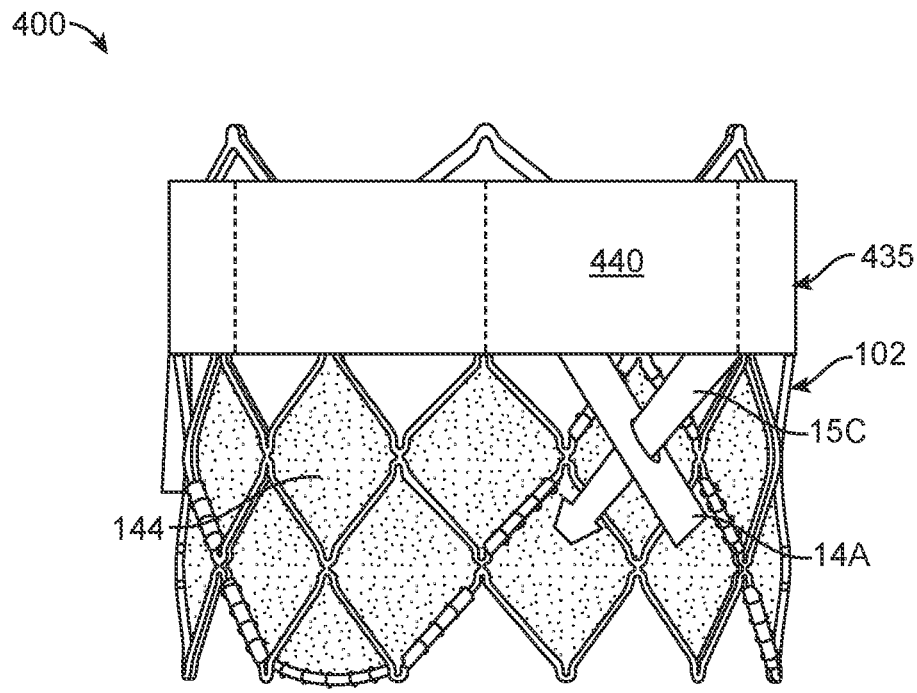
FIG. 6 is a side view of the implant leaflet protection assembly of FIG. 4 further including a leaflet protection tool in accordance with one embodiment.
Figure 7:
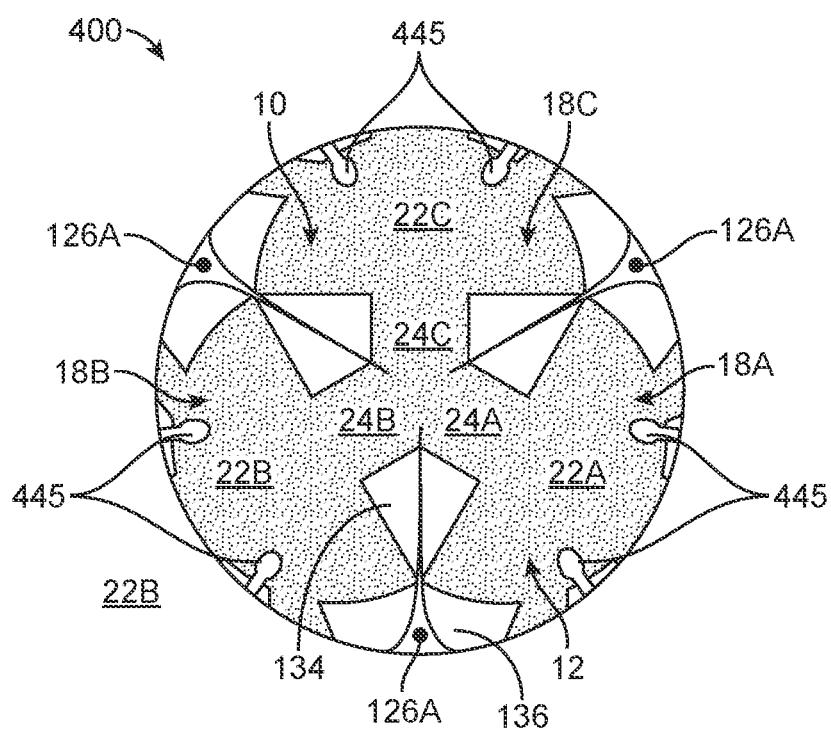
FIG. 7 is an end view of the implant leaflet protection assembly of FIG. 6 in accordance with one embodiment.

FIG. 6 is a side view of implant leaflet protection assembly 400 of FIG. 4 further including a leaflet protection tool 435 in accordance with one embodiment. FIG. 7 is an end view of implant leaflet protection assembly 400 of FIG. 6 in accordance with one embodiment.

Referring now to FIGS. 4-7 together, leaflet protection tool 435 includes an outer portion 440 and protrusions 445 affixed to, integrally formed with, or otherwise coupled to a first surface of outer portion 440. Outer portion 440 may be configured to surround stent 102. Protrusion 445 are configured to minimize and, in some cases, prevent, occurrence of valve leaflets 134 from passing through openings in stent 102 during crimping of transcatheter valve prosthesis 100 in preparation for implantation of transcatheter valve prosthesis 100 into the body of the subject. That is, protrusions 445 may actively push radially inward against valve leaflets 134 to minimize and, in some cases, prevent, pinching of valve leaflets 134 by two or more struts or other structures of stent 102 while transcatheter valve prosthesis 100 is being crimped in preparation for delivery of transcatheter valve prosthesis 100 to an implantation site within the body of the subject. Leaflet protection tool 435 described herein is separate from, and has a structure as a whole that is independent of, the crimping device.

In an embodiment, leaflet protection tool 435 includes six protrusions 445. Each protrusion 445 passes through an opening 125 in stent 102 between axial frame members 126. Protrusion 445, sometimes called petals 445, push valve leaflets 134 inward and away from stent 102 during crimping.

However, absent buffer piece 10, protrusions 445 and/or other structures of transcatheter valve prosthesis 100 such as stent 102 can contact, imprint, abrade, and/or damage valve leaflets 134. Buffer piece 10 and more particularly leaflet cover 12 is a protective buffer piece between protrusions 445/stent 102 and valve leaflets 134 preventing direct contact therebetween. Further, buffer piece 10 holds valve leaflets 134 in place and away from protrusions 445 and stent 102. In this manner, buffer piece 10 prevents contact, imprinting, abrasion, and/or damage to valve leaflets 134 from protrusions 445 and/or other structures such as stent 102 of transcatheter valve prosthesis 100.

For example, during manufacturing, valve leaflets 134 have an abrasion risk from protrusions 445. This abrasion risk includes abrasion during alpha-aminooleic acid anti-calcification treatment (AOA treatment), e.g., from shaking, of valve leaflets 134. The abrasion risk further includes abrasion during shipment and/or storage, e.g., from shaking. Buffer piece 10 reduces and essentially eliminates this abrasion risk.

In one embodiment, buffer piece 10 protects valve leaflets 134 from protrusions 445 during partial crimping. A partial crimp of implant leaflet protection assembly 400 is performed, using a crimping device, to reduce a first diameter of implant leaflet protection assembly 400 to a second diameter smaller than the first diameter. During the partial crimp, protrusion 445 actively pushes radially inward on buffer piece 10 and the underlying valve leaflets 134. By acting as a buffer piece that prevents direct contact between protrusions 445 and valve leaflets 134 during partial crimp, buffer piece 10 minimizes abrasion risk of valve leaflets 134 from protrusions 445. Further, protrusions 445 minimize and/or eliminate the risk of valve leaflets 134 passing through opening(s) in strut 102 and the associated damage during partial crimping.

After partial crimping, buffer piece 10 and leaflet protection tool 435 are removed, e.g., with use of forceps or other suitable tools. After removal of buffer piece 10 and leaflet protection tool 435, a final crimp of transcatheter valve prosthesis 100 is performed using the crimping device to reduce the second diameter to a third diameter smaller than the second diameter in preparation for implantation of transcatheter valve prosthesis 100 into the body of the subject.

However, in another embodiment, buffer piece 10 is removed prior to partial crimping and thus does not prevent direct contact between protrusions 445 and valve leaflets 134 during partial crimp. In accordance with this embodiment, buffer piece 10 still provides protection of valve leaflets 134, e.g., during and after manufacture and transportation as discussed above.

Figure 8:
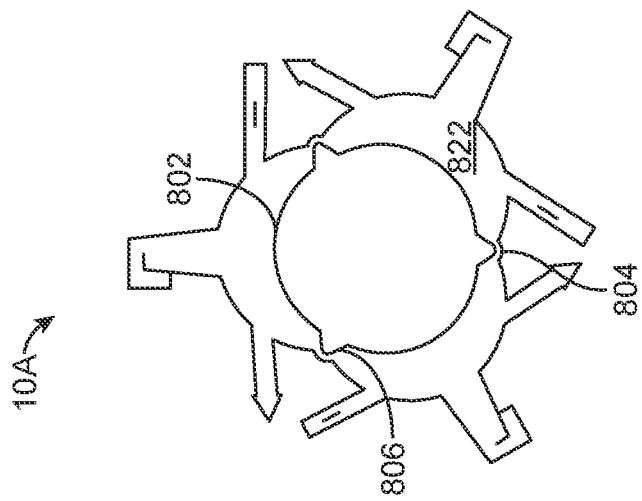
FIG. 8 is a top plan view of a buffer piece in accordance with an embodiment.

FIG. 8 is a top plan view of a buffer piece 10A in accordance with one embodiment. Buffer piece 10A of FIG. 8 is similar to buffer piece 10 of FIG. 1 and only some differences are discussed below.

Referring now to FIG. 8, buffer piece 10A includes a central opening 802. Central opening 802 is a circular opening that allows valve leaflets 134 to stay open when buffer piece 10 is installed. Valve leaflets 134 are normally in an open state and central opening 802 allows valve leaflets 134 to return to the open state. Buffer piece 10A further includes bridges 804 connecting leaflet scallops 822 together so that buffer piece 10A is an integral piece. Further, buffer piece 10A includes indented openings 806 radially extending outwards from opening 802 towards bridges 804. In one embodiment, commissure posts 126A project distally past crowns 120 and indented openings 806 are placed around the outside of the projecting commissure posts 126A.

Figure 9:
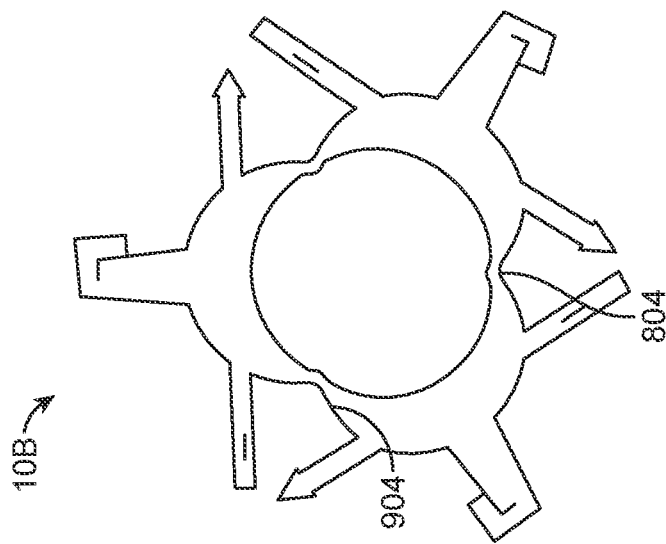
FIG. 9 is a top plan view of a buffer piece in accordance with an embodiment.

FIG. 9 is a top plan view of a buffer piece 10B in accordance with one embodiment. Buffer piece 10B of FIG. 9 is similar to buffer piece 10A of FIG. 8 and only some differences are discussed below. Referring now to FIG. 9, buffer piece 10B includes indented openings 904 radially extending inward towards bridges 804.

Figure 10:
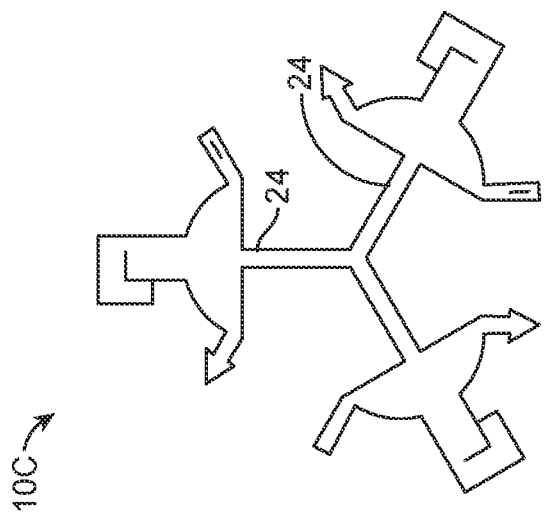
FIG. 10 is a top plan view of a buffer piece in accordance with an embodiment.

FIG. 10 is a top plan view of a buffer piece 10C in accordance with one embodiment. Buffer piece 10C of FIG. 10 is similar to buffer piece 10A of FIG. 8 and only some differences are discussed below. Referring now to FIG. 10, buffer piece 10C includes long leaflet scallop bridges 24. Having long leaflet scallop bridges 24 may facilitate removal of buffer piece 10C without damaging valve leaflets. Further, long leaflet scallop bridges 24 may provide more room for the valve leaflets to open.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

What is claimed is:

1. An assembly comprising:
   a buffer piece comprising:
      a leaflet cover configured to protect valve leaflets of a medical device; and
      a removable attaching structure configured to removably attach the buffer piece to the medical device,
      wherein the removable attaching structure comprises first attaching arms and second attaching arms configured to engage a stent of the medical device, wherein the first attaching arms are configured to be coupled to the second attaching arms around the stent.

2. The assembly of claim 1 wherein the removable attaching structure comprises stent anchor arms configured to engage a stent of the medical device.

3. The assembly of claim 2 wherein the stent anchor arms extend radially outward from the leaflet cover in a plan view of the buffer piece.

4. The assembly of claim 2 wherein the stent anchor arms comprise slots and tabs.

5. The assembly of claim 1 wherein the first attaching arms comprise slots configured to receive the second attaching arms.

6. The assembly of claim 5 wherein the second attaching arms comprise tapered tips configured to facilitate insertion of the second attaching arms into the slots of the first attaching arms.

7. An assembly comprising:
a buffer piece comprising:
a leaflet cover configured to protect valve leaflets of a medical device; and
a removable attaching structure configured to removably attach the buffer piece to the medical device,
wherein the leaflet cover comprises leaflet scallops connected to one another by leaflet scallop bridges,
wherein the buffer piece comprises a center point, the leaflet scallop bridges extending radially inward from the leaflet scallops to be connected at the center point.

8. The assembly of claim 7 wherein the buffer piece is integral.

9. An assembly comprising:
a medical device comprising:
a stent; and
a prosthetic valve connected to the stent, the prosthetic valve comprising valve leaflets; and
a buffer piece comprising:
a leaflet cover protecting the valve leaflets; and
a removable attaching structure removably attaching the buffer piece to the medical device; and
a leaflet protection tool comprising protrusions, the leaflet cover being located between the protrusions and the valve leaflets.

10. The assembly of claim 9 wherein the leaflet cover secures the valve leaflets in place.

11. The assembly of claim 9 wherein the protrusions extend through openings in the stent.

12. An assembly comprising:
a medical device comprising:
a stent; and
a prosthetic valve connected to the stent, the prosthetic valve comprising valve leaflets; and
a buffer piece comprising:
a leaflet cover protecting the valve leaflets; and
a removable attaching structure removably attaching the buffer piece to the medical device,
wherein the leaflet cover is between the valve leaflets and the stent.

13. The assembly of claim 12 wherein the removable attaching structure comprises stent anchor arms configured to engage a stent of the medical device.

14. The assembly of claim 13 wherein the stent anchor arms extend radially outward from the leaflet cover in a plan view of the buffer piece.

15. The assembly of claim 13 wherein the stent anchor arms comprise slots and tabs.

16. The assembly of claim 12 wherein the removable attaching structure comprises first and second attaching arms configured to engage a stent of the medical device.

17. The assembly of claim 16 wherein the first attaching arms are configured to be coupled to the second attaching arms around the stent.

18. The assembly of claim 12 wherein the leaflet cover comprises leaflet scallops connected to one another by leaflet scallop bridges.

19. The assembly of claim 18, wherein the buffer piece comprises a center point, the leaflet scallop bridges extending radially inward from the leaflet scallops to be connected at the center point.

20. The assembly of claim 12, wherein the leaflet cover comprises leaflet scallops circumferentially coupled to each other at bridges.

21. The assembly of claim 20, wherein the bridges include indented openings radially outward or radially inward.

22. The assembly of claim 20, wherein the buffer includes a central opening.

23. The assembly of claim 12, wherein the leaflet cover comprises leaflet scallops, wherein each leaflet scallop is semicircular.

* * * * *